United States Patent
Verhagen et al.

(10) Patent No.: US 11,129,677 B2
(45) Date of Patent: Sep. 28, 2021

(54) LIGHT BASED TISSUE TREATMENT DEVICE

(71) Applicant: KONINKLIJKE PHILIPS N.V., Eindhoven (NL)

(72) Inventors: Rieko Verhagen, Vught (NL); Babu Varghese, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 294 days.

(21) Appl. No.: 16/468,455

(22) PCT Filed: Dec. 5, 2017

(86) PCT No.: PCT/EP2017/081584
§ 371 (c)(1),
(2) Date: Jun. 11, 2019

(87) PCT Pub. No.: WO2018/108637
PCT Pub. Date: Jun. 21, 2018

(65) Prior Publication Data
US 2021/0212765 A1   Jul. 15, 2021

(30) Foreign Application Priority Data
Dec. 12, 2016   (EP) .................................... 16203445

(51) Int. Cl.
*A61B 18/24* (2006.01)
*A61B 18/20* (2006.01)
(Continued)

(52) U.S. Cl.
CPC ............ *A61B 18/24* (2013.01); *A61B 18/203* (2013.01); *H01S 3/025* (2013.01); *H01S 3/094* (2013.01);
(Continued)

(58) Field of Classification Search
CPC .......... A61B 18/24; A61B 2018/20553; H01S 3/025; H01S 3/094; H01S 3/113;
(Continued)

(56) References Cited

U.S. PATENT DOCUMENTS

| 6,676,402 B1 | 1/2004 | Early et al. |
| 2006/0007965 A1 | 1/2006 | Tankovich |

(Continued)

FOREIGN PATENT DOCUMENTS

| EP | 2879249 A2 | 6/2015 |
| WO | WO2005011510 A1 | 2/2005 |

(Continued)

OTHER PUBLICATIONS

PCT International Search Report, International application No. PCT/EP2017/081584, dated Mar. 15, 2018.

*Primary Examiner* — Michael Carter

(57) ABSTRACT

A light based treatment device comprises an optical arrangement at a light exit end of an optical fiber. The optical arrangement includes a master oscillator power amplifier based on a semiconductor optical laser and a crystal optical amplifier. In this way, the peak power provided along the optical fiber can be reduced to prevent damage to the optical fiber, while enabling a sufficiently high pulse power to be delivered for tissue treatment.

16 Claims, 2 Drawing Sheets

(51) Int. Cl.
*H01S 5/02251* (2021.01)
*H01S 5/50* (2006.01)
*H01S 5/02255* (2021.01)
*H01S 5/02253* (2021.01)
*H01S 3/02* (2006.01)
*H01S 3/113* (2006.01)
*H01S 3/094* (2006.01)
*H01S 3/23* (2006.01)

(52) U.S. Cl.
CPC ............ *H01S 3/113* (2013.01); *H01S 3/2308* (2013.01); *H01S 5/02251* (2021.01); *H01S 5/02253* (2021.01); *H01S 5/02255* (2021.01); *H01S 5/50* (2013.01); *A61B 2018/20553* (2017.05)

(58) Field of Classification Search
CPC ............... H01S 3/2308; H01S 5/02251; H01S 5/02255; H01S 5/02253; H01S 5/50
See application file for complete search history.

(56) References Cited

U.S. PATENT DOCUMENTS

| | | |
|---|---|---|
| 2006/0293644 A1 | 12/2006 | Umstadter |
| 2007/0064746 A1 | 3/2007 | Winklhofer et al. |
| 2008/0086118 A1 | 4/2008 | Lai |
| 2009/0227995 A1 | 9/2009 | Bhawalkar |
| 2010/0000485 A1* | 1/2010 | Vogel ............... F02P 23/04 123/143 B |
| 2010/0000486 A1 | 1/2010 | Herden et al. |

FOREIGN PATENT DOCUMENTS

| | | |
|---|---|---|
| WO | WO2007070881 A2 | 6/2007 |
| WO | WO2009144248 A1 | 12/2009 |
| WO | WO2015097679 A1 | 7/2015 |

* cited by examiner

LIGHT BASED TISSUE TREATMENT DEVICE

FIELD OF THE INVENTION

This invention relates to light based tissue treatment devices. In such devices, the light source serves to provide an incident light beam for treating a tissue by creating lesions or other tissue damage. One example is laser induced optical breakdown (LIOB), which is for example used for the treatment of skin tissue or for hair removal. The invention is in particular for fiber-based systems, such as catheter-based systems.

BACKGROUND OF THE INVENTION

Catheter-based laser systems, using optical fibers, are known for in-vivo intra-arterial and cardiac applications. A fiber-based system can also be used when there is need for a fiber coupled high intensity pulsed laser source such as in applications for laser skin care treatment. This may be used where a base station fiber coupled to a hand piece is favored over systems involving articulated arms for guiding the laser light.

Light based skin treatment devices are for example used for wrinkle treatment and for hair cutting. In light based wrinkle treatment, the device creates a focal spot in a dermis layer of the skin to be treated. The power and pulse duration of the laser and the dimension of the focal spot are selected such that a laser induced optical breakdown (LIOB) phenomenon affects the skin in order to stimulate re-growth of skin tissue and, therewith, to reduce wrinkles. In light based hair cutting, the incident light beam is focused inside the hair and the LIOB phenomenon causes the hair to be cut through.

For example, the international patent application published as WO 2005/011510 describes a device for shortening hairs comprising a laser source for generating a laser beam during a predetermined pulse time, an optical system for focusing the laser beam into a focal spot and a laser beam manipulator for positioning the focal spot in a target position. A dimension of the focal spot and a power of the generated laser beam are such that in the focal spot the laser beam has a power density which is above a characteristic threshold value for hair tissue above which, for the predetermine pulse time, a laser induced optical breakdown (LIOB) phenomenon occurs in the hair tissue.

In general, laser induced optical breakdown (LIOB) occurs in media, which are transparent or semi-transparent for the wavelength of the laser beam, when the power density ($W/cm^2$) of the laser beam in the focal spot exceeds a threshold value which is characteristic for the particular medium. Below the threshold value, the particular medium has relatively low linear absorption properties for the particular wavelength of the laser beam. Above the threshold value, the medium has strongly non-linear absorption properties for the particular wavelength of the laser beam, which are the result of ionization of the medium and the formation of plasma. This LIOB phenomenon results in a number of mechanical effects, such as cavitation and the generation of shock waves, which damage the medium in positions surrounding the position of the LIOB phenomenon.

It has been found that the LIOB phenomenon can be used to break and shorten hairs growing from skin. Hair tissue is transparent or semi-transparent for wavelengths between approximately 500 nm and 2000 nm. For each value of the wavelength within this range, LIOB phenomena occur in the hair tissue at the location of the focal spot when the power density ($W/cm^2$) of the laser beam in the focal spot exceeds a threshold value which is characteristic for the hair tissue. Said threshold value is rather close to the threshold value which is characteristic for aqueous media and tissue and is dependent on the pulse time of the laser beam. In particular, the threshold value of the required power density decreases when the pulse time increases.

In order to achieve mechanical effects as a result of the LIOB phenomenon which are sufficiently effective so as to cause significant damage, i.e. at least initial breakage of a hair, a pulse time in the order of, for example, 10 ns suffices. For this value of the pulse time, the threshold value of the power density of the laser beam in the focal spot is in the order of $2*10^{10}$ $W/cm^2$. For the described pulse time and with a sufficiently small dimension of the focal spot obtained, for example, by means of a lens having a sufficiently large numerical aperture, this threshold value can be achieved with a total pulse energy of only a few tenths of a millijoule.

In addition to skin treatment and hair removal, in-body laser based systems also well known for many minimally invasive medical procedures. These procedures typically involve the use of laser energy for creating lesions inside a target tissue area within the body e.g. inside the heart of a patient.

A particular challenge in these types of lesions is that the endothelial layers inside the heart should preferentially not be affected too much in order to avoid blood clotting and the risk of embolisms. Conventional energy based treatments for e.g. arrhythmias typical rely on affecting the heart tissue to destroy or isolate specific sinus nodes but preferentially avoid scarring to the endothelial tissue. Since most of these devices apply the energy through the endothelial tissue, there is a high probability that these will be affected.

Intra-arterial or venous treatment by means of Laser Induced Optical Breakdown (LIOB) has also been reported in which the benefit is exploited that the endothelial tissue is unaffected during the treatment. However, a particular challenge persists in ensuring that the energy is delivered effectively inside the tissue. Effectiveness in this context implies that sufficient intensity is reached inside the tissue at the position where the lesion is to be created.

A particular challenge in that is that if energy is applied to a catheter in a way that would be effective at creating lesion inside the tissue, it will typically destroy the catheter as well. This is quite obvious if one considers that the LIOB process is typically most effective in (semi)transparent media, optical fiber being one of those.

For example, if a light pulse of sufficient intensity for generating LIOB inside tissue is provided (using a master oscillator power amplifier, MOPA, or directly through a flash lamp pumped laser) that pulse would be sufficiently intense that it would destroy any beam quality preserving fiber through the occurrence of LIOB inside the fiber. A fiber based MOPA design typically uses a seed laser and a doped fiber (e.g. Yb+ or other dopants) to amplify the seed laser. However, as soon as the amplification is close to sufficient to generate LIOB inside tissue, the fiber amplifier will be destroyed.

Known approaches for reducing the power of a transmitted pulse include spreading a laser pulse in space or in time to reduce the intensity in the fiber. However, for a fiber-based miniaturized pulse delivery system, these approaches are not practical. In a spatial spreading approach, it is very difficult if not impossible to recover the intensity afterwards due to deterioration of the beam quality during fiber propagation. In a time spreading approach, it is not then practical to recombine the pulse at the fiber tip due to the size of the hardware required.

There is therefore a need for a solution to obtain sufficiently high intensity at a target position inside a tissue using an optical fiber (such as provided by a catheter) based approach while preserving the fiber integrity. There is also a desire to reduce the requirements on the fiber such that simple step-index multimode or similar fibers can be used instead of photonic crystal fibers that would otherwise be required to transport the high intensity pulsed laser light.

SUMMARY OF THE INVENTION

The invention is defined by the claims.

Examples in accordance with a first aspect of the invention provide a light based tissue treatment device comprising:

an optical fiber light guide for receiving a pulsed incident light beam;

an optical arrangement at a light exit end of the optical fiber, comprising:
  a focusing lens having a central region aligned with the incident light beam;
  a graded refractive index lens downstream of the central region;
  a microchip laser oscillator which receives as input pump light the output of the graded refractive index lens;
  an optical amplifier for amplifying the output of the laser oscillator and for providing a pulsed laser treatment output; and
  a reflector for reflecting light passing through the focusing lens around the central region to the optical amplifier to form amplifier pump light.

This arrangement provides a master oscillator power amplifier, MOPA, at the tip of an optical fiber. In this way, the peak power provided along the optical fiber can be reduced to prevent damage to the optical fiber, while enabling a sufficiently high pulse power to be delivered for tissue treatment. The laser oscillator is combined with an optical amplifier to boost the output power. The laser oscillator comprises a microchip laser oscillator (for example Nd:Cr:YAG based) and the optical amplifier comprises a crystal amplifier (for example Nd:YAG based). Thus, optical fiber components are not used to carry the high intensity optical pulses. In this way, sufficient intensity can be provided at the end of the fiber without causing breakdown of the fiber itself.

The microchip laser oscillator preferably comprises a crystal microchip laser oscillator and the optical amplifier comprises a crystal amplifier. In this design, the generation of the high optical power pulses is achieved using crystal components. The use of central light from the optical fiber as the pump input to the laser and using peripheral light as the pump to the optical amplifier provides a compact arrangement which can be provided in a small volume at the end of the optical fiber.

In this device, the pulse intensity is thus generated only in the far tip of the device and not transported along the length of a fiber. The resulting space constraints are in particular addressed by providing a reflector at the tip of the fiber, which ensures that the pump light forms the required focus, such as a line focus, inside the optical amplifier such that the amplifier gain profile overlaps with the central transmission mode (TEM00) mode of the microchip laser oscillator. The laser oscillator functions as a seed oscillator.

The amplifier crystal doping may vary radially to ensure good modal overlap of the laser oscillator signal with the amplifier crystal gain.

The incident light beam which is carried by the fiber is used as the pump light for the microchip laser oscillator (which functions as the seed laser for the amplifier) and also functions as the pump light for the optical amplifier.

The reflector for example comprises a conical reflector for creating a line focus inside the optical amplifier stage. This line focus functions as pump light for the crystal amplifier.

The crystal laser oscillator for example comprises a passively q-switched microchip laser oscillator.

The crystal laser oscillator may comprise a Cr:YAG saturable absorber chip for receiving pump light and a Nd:YAG laser oscillator chip for creating the laser treatment output. The pump light is the pulsed incident light beam as focused by the graded refractive index lens.

The saturable absorber chip for example has an exit surface with a high reflection coating for the wavelength of the pump light. This provides a double passage of pump light through the absorber chip.

The microchip laser oscillator for example has a pump light input surface with an antireflection coating for the wavelength of the pump light and a high reflecting coating for the wavelength of the laser treatment output. In this way, the laser treatment output can only escape from the laser oscillator at the output side.

The pulsed incident light beam for example has a wavelength of 808 nm and the laser treatment output has a wavelength of 1064 nm.

The crystal amplifier may comprise a doped YAG rod.

The optical arrangement may comprise a sapphire body which defines the focusing lens and reflector. In this way, the reflector may be a total internal reflection reflector, thus keeping the size to a minimum and allowing direct contact with the tissue to be treated.

The optical arrangement preferably comprises an output lens at the output of the optical amplifier stage. This is used for forming a focal spot in the tissue to be treated.

The invention also provides a treatment system comprising:

an optical source for providing the pulsed incident light beam; and the device as defined above for receiving the incident light beam and generating the pulsed laser treatment output.

In one example, the optical fiber light guide may comprise a catheter. The system is thus suitable for internal tissue treatment.

In another example, the optical source is part of a base unit, and the device is part of a hand held unit for application against the skin.

BRIEF DESCRIPTION OF THE DRAWINGS

Examples of the invention will now be described in detail with reference to the accompanying drawings, in which.

DETAILED DESCRIPTION OF THE INVENTION

The invention provides a light based treatment device comprising an optical arrangement at a light exit end of an optical fiber. The optical arrangement includes a master oscillator power amplifier based on a semiconductor optical laser and a crystal optical amplifier. In this way, the peak power provided along the optical fiber can be reduced to prevent damage to the optical fiber, while enabling a sufficiently high pulse power to be delivered for tissue treatment. The high pulse power is generated outside the optical fiber and is not transported by an optical fiber.

Before describing the invention in detail, an outline will be given of one example of the type of device to which the invention relates.

Figure 1:
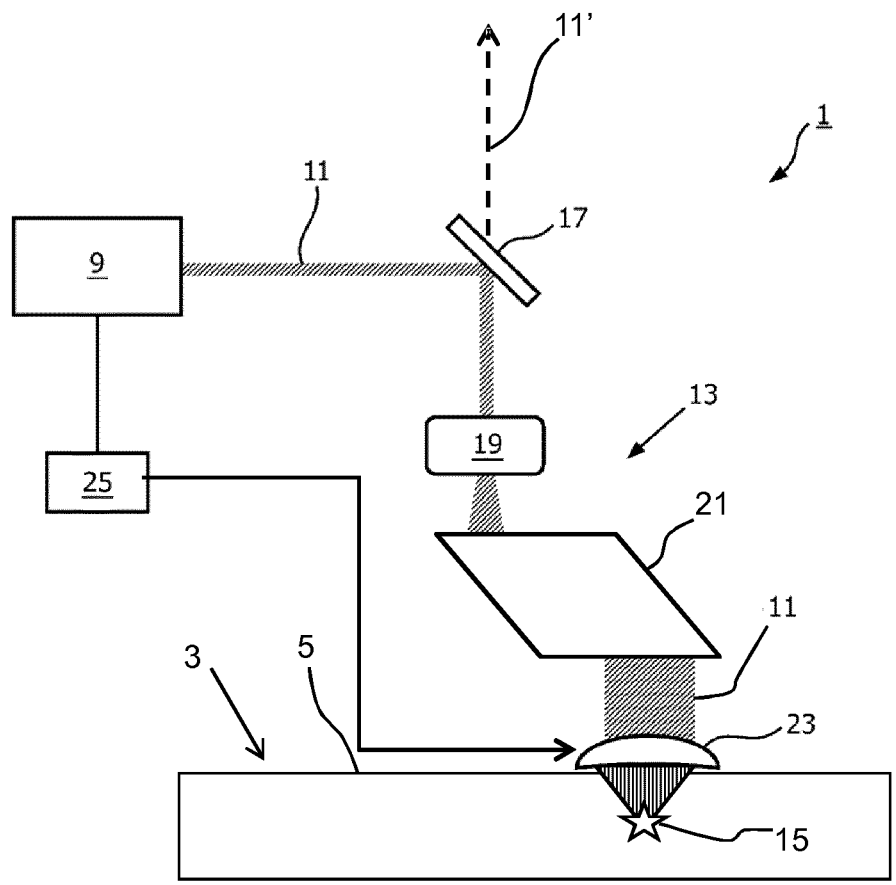
FIG. 1 schematically shows a known LIOB skin treatment device.

FIG. 1 shows a system 1 for treatment of a skin 3 having a surface 5.

The system 1 comprises a light source 9 for generating a laser beam 11 during at least a predetermined pulse time, and it comprises an optical system 13 for focusing the laser beam 11 into a focal spot 15 and for positioning the focal spot 15 in a target position within the skin 3, which is at least partly transparent to the light from the light source 9.

The example of the optical system 13 schematically indicated in FIG. 1 comprises a beam reflecting system 17, a beam shaping system 19, a beam scanning system 21 and a focusing system 23, which systems may comprise one or more mirrors, prisms, beam splitters, polarizers, optical fibers, lenses, apertures, shutters, etc. For example, the scanning system comprises scanning prisms. The beam reflecting system 17 is a dichroic beam splitter. The beam reflecting and beam shaping provide expanding or compressing, and introducing additional convergence or divergence to the beam.

The focusing system has focusing depth selection, beam shaping and focusing and a contact/output window. There is a contour following suspension to maintain contact of the contact/output window.

At least part of the optical system 13 and/or the beam path of the laser beam 11 may be enclosed, e.g. for eye-safety, e.g. comprising opaque tubes and/or one or more optical fibers.

The light source 9 is configured to emit a predetermined number of laser pulses at a predetermined wavelength and with a predetermined pulse duration and repetition rate. The system 1 is configurable such that the target position of the focal spot 15 is beneath the surface of the skin. The dimension of the focal spot 15 and the power of the generated laser beam are such that, in the focal spot 15, the laser beam 11 has a power density, which is above the characteristic threshold value for the skin tissue, above which, for the predetermined pulse time, a laser-induced optical breakdown event occurs.

There may be an articulating arm between the laser source 9 and the beam dichroic beam splitter 17. The beam reflecting system 17 and subsequent components form part of a hand piece. Because of alignment errors in the mirrors of the articulating arm, the beam may be expanded before entering the articulating arm and then compressed afterwards before beam steering and aberration correction.

The skin 3 comprises multiple layers with different optical properties. The epidermis is composed of the outermost layers and forms a waterproof protective barrier. The outermost layer of the epidermis is the stratum corneum which, due to its microscopic fluctuations in roughness, impedes the coupling of light between the device 1 and the skin 3. For this reason, a coupling fluid is preferably provided between the focusing system and the skin, with a refractive index which aims to match that of the skin and/or an exit lens of the focusing system.

Underneath the epidermis, the dermis is situated. The dermis comprises the collagen fibers at which the skin treatment is aimed.

The purpose of the skin treatment is to create the focus 15 of the pulsed laser beam 11 in the collagen of the dermis in order to create microscopic lesions which result in new collagen formation.

The light source 9 is controllable with an optional controller 25, which may provide a user interface. Also, one or more parts of the optical system 13 may be controllable with an optional controller (not shown), which may be integrated with a light source controller 25 to control one or more properties of the target position and/or the focal spot.

Laser beam focusing parameters may be determined by appropriate settings of a beam shaping and/or focusing system, e.g. by adjustment of the numerical aperture of the focusing system. Suitable values for the numerical aperture NA of the focusing system may be chosen from a range $0.05 < NA < nm$, wherein nm is the index of refraction of the medium for the laser wavelength, during operation.

A suitable light source comprises a Q-switched Nd:YAG laser emitting laser pulses at a wavelength of about 1064 nm with a pulse duration of about 5-10 ns, although other lasers, e.g. a Nd:Cr:Yag 3-level laser and/or diode lasers may be used as well. Shorter pulses may also be used, for example sub-nanosecond pulses, for example down to tens or hundreds of picoseconds, such as 100 ps. The small size of the microchip laser makes this possible.

The beam reflecting system 17 comprises a dichroic beam splitter which reflects the laser light but passes visible wavelength light. Thus, received visible wavelength light from the skin 3 is captured by the optical system and is provided as a feedback signal 11' which can be used for controlling the system either manually or automatically.

The invention relates to a system in which the treatment part of the device is instead connected to the laser source by an optical fiber. In this way, the treatment part may be at the end of a catheter thus enabling internal treatment, or it may be a hand-held portable device, thereby avoiding the need for expensive and bulky articulation arms.

The system of the invention makes use of a two-step approach whereby a complete master-oscillator power amplifier and optical system is integrated into a fiber tip in the form of a so-called master oscillator power amplifier (MOPA) layout. The fiber itself is used for guiding pump laser light from outside the body to the tip where the pump light is converted to short intense laser pulses by a combination of a number of oscillator crystals and an optical system consisting of lenses and mirrors. Although the average optical power entering the fiber is significantly higher, the peak power can be lower by 6 to 7 orders of magnitude, ensuring that the fiber can effectively support the light without causing immediate breakdown.

Figure 2:
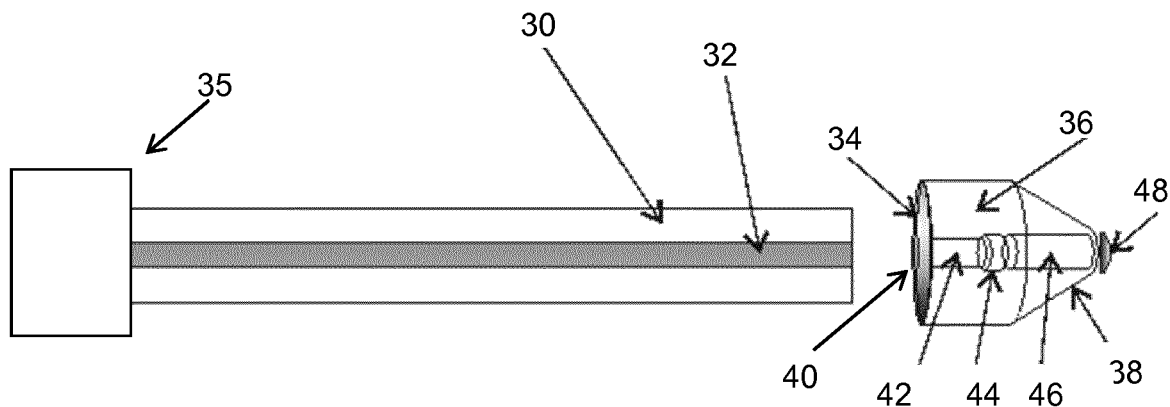
FIG. 2 shows a light based treatment device.

FIG. 2 shows an example of an implementation of the system.

The system comprises a catheter 30 containing a light guide 32 which guides pump laser light from a diode laser source 35 for example at 808 nm.

The laser light diverges from the fiber tip and then is incident on a lens surface 34 of an optical element 36.

The optical element 36 is formed as a solid body, which at the light input side has an aspherical lens surface 34 and at the output surface has a conical reflector 38. The lens surface has a central region 40 and an outer region radially outside the central region. The central region may be a through hole 40. Downstream of the central region is a graded refractive index (GRIN) lens 42, a passively q-switched microchip laser oscillator 44 and a crystal optical amplifier 46.

The optical element may comprise a body with a central through hole in which the lens 42, oscillator 44 and amplifier 46 are formed. The front end of the through hole then forms the central region and front end of the solid body around the though hole forms the lens surface. There may instead be a separate lens element at the body may then have a planar front surface.

The generated laser light emerges from the optical element 36 and is focused by an aspherical lens 48 to form a tight spot inside the tissue. This spot is used for creating lesions or providing LIOB.

To generate the laser pulses, the central part of the incident pump light is collected and focused by the GRIN lens 42 into the laser oscillator chip 44.

The peripheral part of the incident pump light is initially collimated by the lens surface 34 and is then deflected by the conical reflector surface 38 to form a line focus centered inside the crystal optical amplifier 46.

The line focus inside the crystal amplifier ensures that the amplifier gain profile overlaps with the central transmission mode (TEM00) of the microchip laser oscillator. The amplifier crystal doping may vary radially to ensure good modal overlap of the laser oscillator signal with the amplifier crystal gain.

Figure 3:
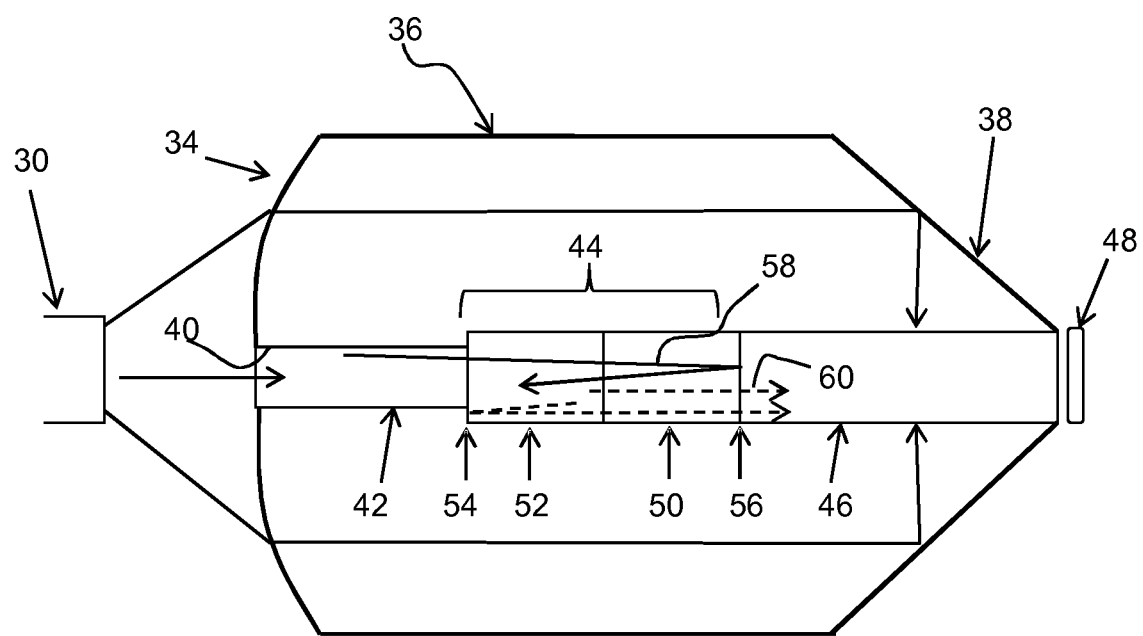
FIG. 3 shows the optical components of the device of FIG. 2 in more detail.

FIG. 3 shows the components in more detail.

The laser oscillator chip 44 consists of a double stack of a Cr:YAG saturable absorber chip 50 and a high doped Nd:YAG laser oscillator chip 52 fused together.

The pump beam entry surface 54 of the oscillator chip 52 is polished and provided with an antireflection coating for the 808 nm pump beam and has a high reflection coating for the 1064 nm laser beam.

The output side 56 of the saturable absorber chip 50 has a high reflection coating for 808 nm to exploit a double passage of the pump light 58 through the chip. The reflectivity at 1064 nm can be engineered to allow for optimal pulse duration and intensity properties of the generated light 60.

The crystal amplifier 46 is pumped by the peripheral part of the light emitted by the fiber that is collimated by lens surface 34 and deflected by the conical mirror surface 38. The conical mirror may either be coated to ensure reflection of the 808 nm pump laser light or it could exploit the principle of total internal reflection, depending on the refractive index difference between the medium of the optical element 36 and the surrounding medium.

If the optical element 36 is made of sapphire (refractive index n=1.76) it is possible to use the tip in direct contact with blood and tissue without any coatings, just relying on the principle of total internal reflection to deflect the light.

The amplifier crystal itself could be a low Neodymium doped YAG rod. The doping may be homogeneous or alternatively it could employ either radially or longitudinally varying doping concentrations. In particular, radial distributions could be employed to confine the gain to the center of the crystal to ensure good overlap of the pump light with the doped area of the crystal and to ensure proper mode overlap of the pump and laser light. The various surfaces of the rod can be coated to provide minimal losses to the pump and laser wavelength where appropriate.

The ratio of the amount of peripheral light versus the amount of central pump light can easily be tuned by varying the distance of the optical element 36 to the fiber 30. Optionally, the lens surfaces 34 and 48 may be implemented directly in the optical element 36 or they could be manufactured separately and fused/glued to the body during manufacture.

The design can easily be miniaturized and is very easy to align and is thermally stable due to its symmetry. Moreover, the use of sapphire as the main body of the laser generator ensures it will be easily cooled by the surrounding blood flow. Typical diameters of the optical element 4 will be less than 1cm.

The fiber tip mounted MOPA laser design may be employed effectively for generating sub-nanosecond laser pulses with pulse energies of several tens of microjoules up to a few millijoules per pulse, for a single laser pulse up to several hundreds of pulses per second.

The circular symmetry and optimized thermal design enables good beam quality, which is essential for obtaining tight focusing that is necessary for the creation of a LIOB event in tissue.

The invention can be applied anywhere there is need for high peak power and high intensity laser pulses in areas that can only be made accessible through fiber-optic endoscopes and/or fiber based light guides. These could be related to in-vivo endoscopic applications for example. In the area of handheld devices, the invention may enable the use of a fiber coupled laser diode in a base station which is connected by means of the fiber a lightweight handpiece which houses the laser crystals and focusing optics. In this way the use of cumbersome and expensive articulated arms for guiding the high intensity laser pulses can be avoided.

The example above is based on a Cr:YAG crystal saturable absorber chip 50 and a high doped Nd:YAG laser oscillator chip. However, other microchip based lasers and other saturable absorbers may be used. Semiconductor saturable absorbers may also be used.

The example above is based on a Neodymium doped YAG rod as the crystal amplifier. Other examples are Yb:YAG, Nd:Yb:YAG and Yb:Cr:YAB.

The examples described above make use of a crystal laser oscillator and amplifier, in particular to achieve the desired pulse energy. However, semiconductor microchip laser oscillators (and corresponding semiconductor optical amplifiers) may instead be used, if current or future designs have suitable performance.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A light based tissue treatment device comprising:
   an optical fiber light guide for receiving a pulsed incident light beam;
   an optical arrangement at a light exit end of the optical fiber, comprising:

a focusing lens having a central region aligned with the incident light beam;
a graded refractive index lens downstream of the central region;
a microchip laser oscillator which receives as input pump light the output of the graded refractive index lens;
an optical amplifier for amplifying the output of the microchip laser oscillator and for providing a pulsed laser treatment output; and
a reflector for reflecting light passing through the focusing lens around the central region to the optical amplifier to form amplifier pump light.

2. The device as claimed in claim 1, wherein the microchip laser oscillator comprises a crystal laser oscillator, and the optical amplifier comprises a crystal amplifier.

3. The device as claimed in claim 1, wherein the reflector comprises a conical reflector for creating a line focus inside the optical amplifier.

4. The device as claimed in claim 1, wherein a gain profile of the optical amplifier overlaps with a central transmission mode of the microchip laser oscillator.

5. The device as claimed in claim 1, wherein the microchip laser oscillator comprises a passively q-switched microchip laser oscillator.

6. The device as claimed in claim 5, wherein the laser oscillator comprises a Cr:YAG saturable absorber chip for receiving a pump light and a Nd:YAG laser oscillator chip for creating the laser treatment output.

7. The device as claimed in claim 6, wherein the saturable absorber chip has an exit surface with a high reflection coating for the wavelength of the pump light.

8. The device as claimed in claim 6, wherein the microchip laser oscillator has a pump light input surface with an antireflection coating for the wavelength of the pump light and a high reflecting coating for the wavelength of the laser treatment output.

9. The device as claimed in claim 1, wherein the pulsed incident light beam has a wavelength of approximately 808 nm, and the laser treatment output has a wavelength of approximately 1064 nm.

10. The device as claimed in claim 1, wherein the optical amplifier comprises a doped YAG rod.

11. The device as claimed in claim 1, wherein the optical arrangement comprises a sapphire body which defines the focusing lens and reflector.

12. The device as claimed in claim 1, wherein the optical arrangement comprises an output lens at the output of the crystal optical amplifier.

13. The device as claimed in claim 1, wherein the central region comprises an aperture.

14. A treatment system, comprising:
an optical source for providing a pulsed incident light beam; and
a light based tissue treatment device comprising:
an optical fiber light guide for receiving the pulsed incident light beam; and
an optical arrangement at a light exit end of the optical fiber, comprising:
a focusing lens having a central region aligned with the incident light beam:
a graded refractive index lens downstream of the central region;
a microchip laser oscillator which receives as input pump light the output of the graded refractive index lens;
an optical amplifier for amplifying the output of the microchip laser oscillator and for providing a pulsed laser treatment output; and
a reflector for reflecting light passing through the focusing lens around the central region to the optical amplifier to form amplifier pump light.

15. The system as claimed in claim 14, wherein: the light based tissue treatment device is a part of a hand held unit for application against the skin.

16. The system as claimed in claim 14, wherein the optical fiber light guide comprises a catheter.

* * * * *